United States Patent
Pontoppidan et al.

(10) Patent No.: US 9,210,517 B2
(45) Date of Patent: Dec. 8, 2015

(54) HEARING ASSISTANCE DEVICE WITH BRAIN COMPUTER INTERFACE

(71) Applicant: Oticon A/S, Smørum (DK)

(72) Inventors: Niels Henrik Pontoppidan, Smørum (DK); Thomas Lunner, Smørum (DK); Michael Syskind Pedersen, Smørum (DK); Lars Ivar Hauschultz, Valby (DK); Povl Koch, Smørum (DK); Graham Naylor, Smørum (DK); Eline Borch Petersen, Smørum (DK)

(73) Assignee: OTICON A/S, Smorum (DK)

( * ) Notice: Subject to any disclaimer, the term of this patent is extended or adjusted under 35 U.S.C. 154(b) by 0 days.

(21) Appl. No.: 14/303,844

(22) Filed: Jun. 13, 2014

(65) Prior Publication Data

US 2014/0369537 A1     Dec. 18, 2014

(30) Foreign Application Priority Data

Jun. 14, 2013   (EP) ..................................... 13172066

(51) Int. Cl.
*H04R 25/00* (2006.01)
*A61B 5/0478* (2006.01)
(Continued)

(52) U.S. Cl.
CPC .............. *H04R 25/00* (2013.01); *A61B 5/0478* (2013.01); *A61B 5/04845* (2013.01); *A61B 5/6817* (2013.01); *G06F 3/013* (2013.01); *G06F 3/015* (2013.01); *G06K 9/00604* (2013.01);
(Continued)

(58) Field of Classification Search
CPC ...... H04R 25/00; H04R 25/55; H04R 25/558; H04R 25/60; H04R 25/65; H04R 1/105; H04R 2225/021; H04R 2225/63

USPC ................... 381/312, 322, 324, 330, 314–315
See application file for complete search history.

(56) References Cited

U.S. PATENT DOCUMENTS

| | | |
|---|---|---|
| 4,689,818 A | 8/1987 | Ammitzboll |
| 5,680,467 A | 10/1997 | Hansen |

(Continued)

FOREIGN PATENT DOCUMENTS

| | | |
|---|---|---|
| CA | 2297344 A1 | 8/2000 |
| EP | 2200342 A1 | 6/2010 |

(Continued)

OTHER PUBLICATIONS

Bergasa et al., "Real-Time System for Monitoring Driver Vigilance", IEEE Transactions on Intelligent Transportation Systems, Mar. 2006, vol. 7, No. 1, pp. 63-77.

(Continued)

*Primary Examiner* — Suhan Ni
(74) *Attorney, Agent, or Firm* — Birch, Stewart, Kolasch & Birch, LLP

(57) ABSTRACT

The present disclosure relates to communication devices. Such devices may comprise input for receiving sound signal to be processed and presented to a user, and output for outputting the processed signal to a user perceivable as sound. Such processing may be performed by use of a processor for processing the sound signal in dependence of a setting or a set of setting to compensate a hearing loss profile. Further, the communication device may comprise a bio-signal acquisition and amplifier component in communication with a user interface for providing the bio-signals as input to the user interface, the user interface controlling the setting or set of setting for operation of the communication device.

18 Claims, 7 Drawing Sheets

(51) Int. Cl.
*A61B 5/0484* (2006.01)
*G06F 3/01* (2006.01)
*G06K 9/00* (2006.01)
*A61B 5/00* (2006.01)
*A61B 5/048* (2006.01)
*A61B 5/0482* (2006.01)
*A61B 5/12* (2006.01)

(52) U.S. Cl.
CPC ............... *H04R25/505* (2013.01); *A61B 5/048* (2013.01); *A61B 5/0482* (2013.01); *A61B 5/121* (2013.01); *A61B 5/6868* (2013.01); *H04R 25/40* (2013.01); *H04R 25/453* (2013.01); *H04R 25/552* (2013.01); *H04R 25/70* (2013.01); *H04R 2225/41* (2013.01); *H04R 2225/43* (2013.01); *H04R 2225/61* (2013.01)

(56) References Cited

U.S. PATENT DOCUMENTS

| | | | |
|---|---|---|---|
| 5,999,631 | A | 12/1999 | Porayath et al. |
| 2005/0175218 | A1 | 8/2005 | Vertegaal et al. |
| 2010/0074460 | A1 | 3/2010 | Marzetta |
| 2012/0177233 | A1* | 7/2012 | Kidmose et al. ............. 381/314 |
| 2013/0343585 | A1* | 12/2013 | Bennett et al. ............... 381/315 |

FOREIGN PATENT DOCUMENTS

| | | |
|---|---|---|
| EP | 2508945 A1 | 10/2012 |
| EP | 2560412 A1 | 2/2013 |
| WO | WO 2011/000375 A1 | 1/2011 |
| WO | WO 2011/006681 A1 | 1/2011 |
| WO | WO 2013/017169 A1 | 2/2013 |

OTHER PUBLICATIONS

Caffier et al., "Experimental evaluation of eye-blink parameters as a drowsiness measure", Eur J Appl Physiol, Mar. 14, 2003, vol. 89, pp. 319-325.

Dyrlund et al., "Acoustic feedback margin improvements in hearing instruments using a prototype DFS (digital feedback suppression) system", Scandinavian Audiology, 1991, vol. 20, pp. 49-53.

Engebretson et al., "Properties of an adaptive feedback equalization algorithm", Journal of Rehabilitation Research and Development, 1993, vol. 30, No. 1, pp. 8-16.

Liao et al., "Gaming control using a wearable and wireless EEG-based brain-computer interface device with novel dry foam-based sensors", Journal of NeuroEngineering and Rehabilitation, Jan. 28, 2012, vol. 9, No. 5, pp. 1-11.

Singh et al., "A review on electrooculography", International Journal of Advanced Engineering Technology, Oct.-Dec. 2012, vol. 3, Issue 4, pp. 115-122.

* cited by examiner

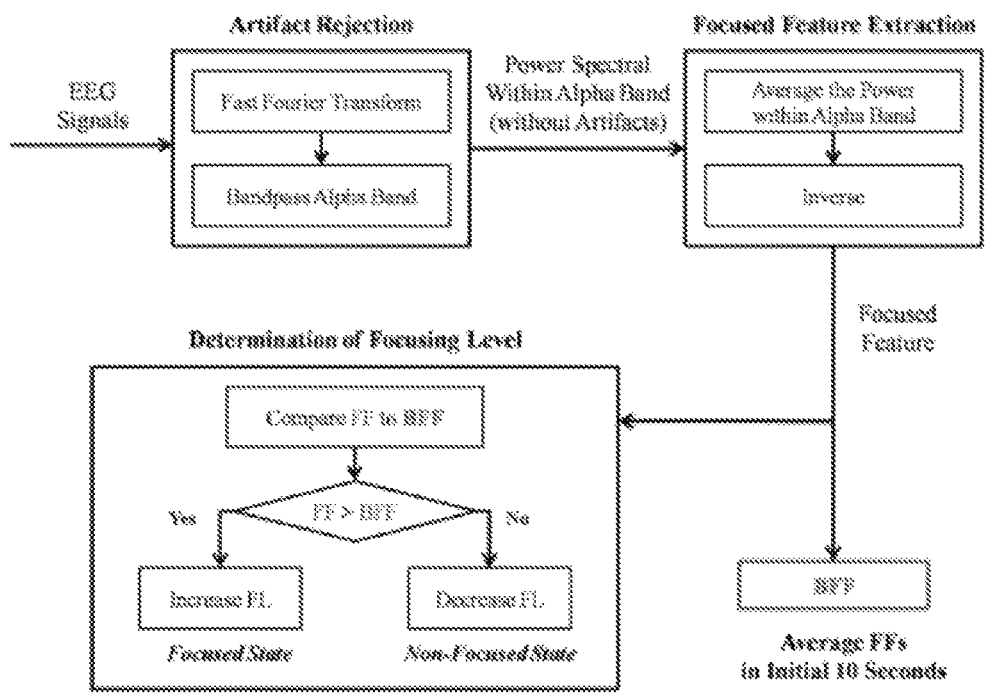
FIG 6
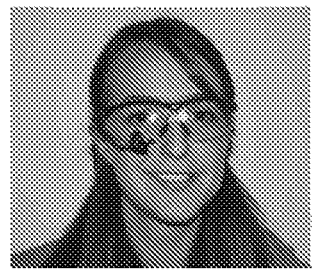 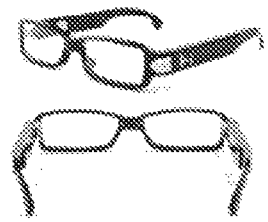
FIG. 7A    FIG. 7B

HEARING ASSISTANCE DEVICE WITH BRAIN COMPUTER INTERFACE

TECHNICAL FIELD

The present application relates to controlling a hearing assistance device using a brain computer interface. The application furthermore relates to controlling a hearing assistance device using an eye monitoring interface.

Embodiments of the disclosure may e.g. be useful in applications such as hearing aid devices, headsets, ear phones, active ear protection systems, handsfree telephone systems, mobile telephones, teleconferencing systems, public address systems, karaoke systems, classroom amplification systems, etc.

SUMMARY

An object of the present invention is to controlling a hearing assisting device.

Objects of the application are achieved by the invention described in the accompanying claims and as described in the following.

The present disclosure includes description of a communication device, which may comprise an input for receiving a sound signal to be processed and presented to a user, and an output for outputting a signal to a user perceivable as sound and a processor for processing the sound signal in dependence of a setting or a set of setting to compensate a hearing loss profile. Such a device may be a hearing aid, a headset or any other suitable sound processing device, which advantageously may be configured to be placed at or in an ear, e.g. behind the pinna or at least partly in the ear canal. Further, the communication device may include a bio-signal acquisition and amplifier component in communication with a user interface for providing the bio-signals as input to the user interface, the user interface controlling the setting or set of setting for operation of the communication device. This allows the bio-signal component to detect and/or record different electrical signal originating from physical movements and/or thought patterns relating to movements. This will allow a user, i.e. a wearer, to for instance think about moving the right arm, which will then cause a specific pattern of EEG signals that the bio-signal component may then register. This registered bio-signal may then be processed for identification and/or classification, e.g. determining if the signal originates from eye movement, such as an EOG-signal and/or blinking, a thought pattern, e.g. wearer thinking of moving an arm or turning the head, or physical movement of limb.

The ear EEG electrode may advantageously be comprised in a mould configured specifically for the wearers ear canal. This will make the EEG electrode more comfortable to wear, and improve the contact between EEG electrode pad and ear canal, also because the position of the EEG electrode in the ear canal will be more consistent each time the ear EEG electrode is placed by the wearer. The EEG electrode may alternatively be contact-free capacitive electrodes.

The bio-signal amplifier and acquisition component may comprise an ear EEG electrode may be configured to be inserted into an ear canal or on a skin-part of the head of a wearer or bio-signal amplifier and acquisition component may comprise an implantable EEG electrode configured to be placed under the skin at the head of a wearer or an implantable EEG electrode configured to be placed on the ear canal.

The EEG electrode may be configured to pick up intended space gestures constituting an input from a wearer. Advantageously the bio-signal may represent eye movement and/or brain activity signals. These may then be intrepreted by the system as inputs, e.g. by classifying them as specific movements or movement patterns. One document dealing with space gestures is LaFleur et. al. 'Quadcopter control in three-dimensional space using a noninvasive motor imagery-based brain-computer interface', 2013 J. Neural Eng. 10 046003.

The bio-signal amplifier and acquisition component may include a wearable camera for eye-tracking. This allow non-intrusive monitoring of the eyes. A camera may be combined with an EEG component, which may further reduce the risk of misinterpreting inputs from the wearer.

The communication system may further comprise an alarm device configured to provide an alarm signal if the bio-signal from the bio-signal acquisition and amplifier is determined to represent a cognitive state classified as a state deserving attention, or possibly even a state which may be dangerous to the persons health, possibly combined with knowledge of the persons surroundings. This could then be used to alert the wearer or even another person, such as a caretaker, that the wearer is entering a state where attention is needed or no longer needed, e.g. while driving a car the wearer may become drowsy, or the wearer may experience a heart attack which needs to be communicated to other persons so they may take appropriate action. Further, for example, the device may send a signal to the care-home supervisor that the patient in room 23 is now asleep, or is no longer asleep.

The present disclosure also includes a communication system comprising two communication devices as described in other sections of the present disclosure. Each of such two communication devices may then be configured to be placed behind or at an ear of the wearer and each communication device may then comprise a brain-computer interface comprising an ear EEG electrode configured to be inserted in a respective ear canal of a wearer.

The present disclosure further includes a method of controlling communication device comprising an input for receiving a sound signal to be processed and presented to a user, and an output for outputting a signal to a user perceivable as sound, a processor for processing the sound signal in dependence of a setting or a set of setting to compensate a hearing loss profile, and a bio-signal acquisition and amplifier component in communication with a user interface for providing the bio-signals as input to the user interface, the user interface controlling the setting or set of setting for operation of the communication device. The method may comprise obtaining via bio-signal acquisition and amplifier component a bio-signal representing a gesture. The method may comprise analysing the bio-signal for recognising an intended space gesture. The method may comprise processing the intended space gesture to translate it to an input for the user interface.

A user may think of a target direction and the intended space gesture may then be determined, and the method may then comprise using the gesture signal as input for the user interface.

A user may move a limb in a target direction and the intended space gesture may be detected or a user may move one or both eyes in a target direction and the intended space gesture may be detected.

A user may imagine moving a limb in a target direction and the intended space gesture may then be detected. A user may imagine moving one or both eyes in a target direction and the intended space gesture may then be detected based on this.

The processing of the bio-signal may be translated into control of directionality pattern of a microphone beamformer, which may be directing the beamformer in an intended direction based in the bio-signal input. The processing of the bio-signal may be translated into a change of current program for sound processing, e.g. more or less noise suppression, enabling or ending a music processing program.

A wearable camera may be directed at the eye of the user, which may then be used to determine the gesture signal. A combination of several types of sensors, e.g. EEG sensor and camera, may be envisioned.

A fatigue level may be determined via the bio-signal, e.g. using a camera and basing the determination on images of the pupil, optionally by determining the angular orientation of the pupil and/or the size of the pupil.

A Hearing Assistance Device:

In a first aspect of the present invention, the object is achieved by a hearing assistive device comprising brain interface means adapted to control the hearing assistive device according to brain signals.

In a second aspect of the present invention, the object is achieved by a hearing assistive device comprising an eye monitoring means adapted to determine the angular orientation of the pupil as well as the size.

These aspects and embodiments may be combined with any feature or features and/or other aspects and/or embodiments mentioned throughout the present specification.

In an embodiment, the hearing assistance device is adapted to provide a frequency dependent gain to compensate for a hearing loss of a user. In an embodiment, the hearing assistance device comprises a signal processing unit for enhancing the input signals and providing a processed output signal.

In an embodiment, the hearing assistance device comprises an output transducer for converting an electric signal to a stimulus perceived by the user as an acoustic signal. In an embodiment, the output transducer comprises a number of electrodes of a cochlear implant or a vibrator of a bone conducting hearing device. In an embodiment, the output transducer comprises a receiver (speaker) for providing the stimulus as an acoustic signal to the user.

In an embodiment, the hearing assistance device comprises an input transducer for converting an input sound to an electric input signal. In an embodiment, the hearing assistance device comprises a directional microphone system adapted to enhance a target acoustic source among a multitude of acoustic sources in the local environment of the user wearing the hearing assistance device. In an embodiment, the directional system is adapted to detect (such as adaptively detect) from which direction a particular part of the microphone signal originates. This can be achieved in various different ways as e.g. described in the prior art.

In an embodiment, the hearing assistance device comprises an antenna and transceiver circuitry for wirelessly receiving a direct electric input signal from another device, e.g. a communication device or another hearing assistance device. In an embodiment, the hearing assistance device comprises a (possibly standardized) electric interface (e.g. in the form of a connector) for receiving a wired direct electric input signal from another device, e.g. a communication device or another hearing assistance device. In an embodiment, the direct electric input signal represents or comprises an audio signal and/or a control signal and/or an information signal. In an embodiment, the hearing assistance device comprises demodulation circuitry for demodulating the received direct electric input to provide the direct electric input signal representing an audio signal and/or a control signal e.g. for setting an operational parameter (e.g. volume) and/or a processing parameter of the hearing assistance device. In general, the wireless link established by a transmitter and antenna and transceiver circuitry of the hearing assistance device can be of any type. In an embodiment, the wireless link is used under power constraints, e.g. in that the hearing assistance device comprises a portable (typically battery driven) device. In an embodiment, the wireless link is a link based on near-field communication, e.g. an inductive link based on an inductive coupling between antenna coils of transmitter and receiver parts. In another embodiment, the wireless link is based on far-field, electromagnetic radiation. In an embodiment, the communication via the wireless link is arranged according to a specific modulation scheme, e.g. an analogue modulation scheme, such as FM (frequency modulation) or AM (amplitude modulation) or PM (phase modulation), or a digital modulation scheme, such as ASK (amplitude shift keying), e.g. On-Off keying, FSK (frequency shift keying), PSK (phase shift keying) or QAM (quadrature amplitude modulation).

In an embodiment, the communication between the hearing assistance device and the other device is in the base band (audio frequency range, e.g. between 0 and 20 kHz). Preferably, communication between the hearing assistance device and the other device is based on some sort of modulation at frequencies above 100 kHz. Preferably, frequencies used to establish communication between the hearing assistance device and the other device is below 50 GHz, e.g. located in a range from 50 MHz to 50 GHz, e.g. above 300 MHz, e.g. in an ISM range above 300 MHz, e.g. in the 900 MHz range or in the 2.4 GHz range. The communication protocol may for instance be Bluetooth or Bluetooth low-energy, or based on these protocols.

In an embodiment, the hearing assistance device and/or the communication device comprises an electrically small antenna. An 'electrically small antenna' is in the present context taken to mean that the spatial extension of the antenna (e.g. the maximum physical dimension in any direction) is much smaller than the wavelength $\lambda_{Tx}$ of the transmitted electric signal. In an embodiment, the spatial extension of the antenna is a factor of 10, or 50 or 100 or more, or a factor of 1 000 or more, smaller than the carrier wavelength $\lambda_{Tx}$ of the transmitted signal. In an embodiment, the hearing assistance device is a relatively small device. The term 'a relatively small device' is in the present context taken to mean a device whose maximum physical dimension (and thus of an antenna for providing a wireless interface to the device) is smaller than 10 cm, such as smaller than 5 cm. In an embodiment 'a relatively small device' is a device whose maximum physical dimension is much smaller (e.g. more than 3 times, such as more than 10 times smaller, such as more than 20 times small) than the operating wavelength of a wireless interface to which the antenna is intended (ideally an antenna for radiation of electromagnetic waves at a given frequency should be larger than or equal to half the wavelength of the radiated waves at that frequency). At 860 MHz, the wavelength in vacuum is around 35 cm. At 2.4 GHz, the wavelength in vacuum is around 12 cm. In an embodiment, the hearing assistance device has a maximum outer dimension of the order of 0.15 m (e.g. a handheld mobile telephone). In an embodiment, the hearing assistance device has a maximum outer dimension of the order of 0.08 m (e.g. a head set). In an embodiment, the hearing assistance device has a maximum outer dimension of the order of 0.04 m (e.g. a hearing instrument).

In an embodiment, the hearing assistance device is portable device, e.g. a device comprising a local energy source, e.g. a battery, e.g. a rechargeable battery. In an embodiment, the hearing assistance device is a low power device. The term 'low power device' is in the present context taken to mean a device whose energy budget is restricted, e.g. because it is a portable device, e.g. comprising an energy source (e.g. of limited size, e.g. with a maximum capacity of 1000 mAh, such as 500 mAh), which—without being exchanged or recharged—is of limited duration (the limited duration being e.g. of the order of hours or days, e.g. max. 1 or 3 or 7 or 10 days (during normal operation of the device), such duration being limited compared to the expected life time of the device). In an embodiment, the energy source of the hearing assistance device is removed of disconnected, when the hearing assistance device is not in operational use (whereby data that are not stored in a non-volatile memory are lost).

In an embodiment, the hearing assistance device comprises a forward or signal path between an input transducer (microphone system and/or direct electric input (e.g. a wireless receiver)) and an output transducer. In an embodiment, the signal processing unit is located in the forward path. In an embodiment, the signal processing unit is adapted to provide a frequency dependent gain according to a user's particular needs. In an embodiment, the hearing assistance device comprises an analysis path comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain.

In an embodiment, an analogue electric signal representing an acoustic signal is converted to a digital audio signal in an analogue-to-digital (AD) conversion process, where the analogue signal is sampled with a predefined sampling frequency or rate $f_s$, $f_s$ being e.g. in the range from 8 kHz to 40 kHz (adapted to the particular needs of the application) to provide digital samples $x_n$ (or x[n]) at discrete points in time $t_n$ (or n), each audio sample representing the value of the acoustic signal at $t_n$ by a predefined number $N_s$ of bits, $N_s$ being e.g. in the range from 1 to 16 bits.

A digital sample x has a length in time of $1/f_s$, e.g. 50 µs, for $f_s$=20 kHz. In an embodiment, a number of audio samples are arranged in a time frame. In an embodiment, a time frame comprises 64 audio data samples. Other frame lengths may be used depending on the practical application.

In an embodiment, the hearing assistance devices comprise an analogue-to-digital (AD) converter to digitize an analogue input with a predefined sampling rate, e.g. 20 kHz. In an embodiment, the hearing assistance devices comprise a digital-to-analogue (DA) converter to convert a digital signal to an analogue output signal, e.g. for being presented to a user via an output transducer.

In an embodiment, the hearing assistance device, e.g. the microphone unit, and or the transceiver unit comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain. In an embodiment, the frequency range considered by the hearing assistance device from a minimum frequency $f_{min}$ to a maximum frequency $f_{max}$ comprises a part of the typical human audible frequency range from 20 Hz to 20 kHz, e.g. a part of the range from 20 Hz to 12 kHz. In an embodiment, a signal of the forward and/or analysis path of the hearing assistance device is split into a number NI of frequency bands, where NI is e.g. larger than 5, such as larger than 10, such as larger than 50, such as larger than 100, such as larger than 500, at least some of which are processed individually. In an embodiment, the hearing assistance device is/are adapted to process a signal of the forward and/or analysis path in a number NP of different frequency channels (NP≤NI). The frequency channels may be uniform or non-uniform in width (e.g. increasing in width with frequency), overlapping or non-overlapping.

In an embodiment, the hearing assistance device comprises a level detector (LD) for determining the level of an input signal (e.g. on a band level and/or of the full (wide band) signal). The input level of the electric microphone signal picked up from the user's acoustic environment is e.g. a classifier of the environment. In an embodiment, the level detector is adapted to classify a current acoustic environment of the user according to a number of different (e.g. average) signal levels, e.g. as a HIGH-LEVEL or LOW-LEVEL environment.

In a particular embodiment, the hearing assistance device comprises a voice detector (VD) for determining whether or not an input signal comprises a voice signal (at a given point in time). A voice signal is in the present context taken to include a speech signal from a human being. It may also include other forms of utterances generated by the human speech system (e.g. singing). In an embodiment, the voice detector unit is adapted to classify a current acoustic environment of the user as a VOICE or NO-VOICE environment. This has the advantage that time segments of the electric microphone signal comprising human utterances (e.g. speech) in the user's environment can be identified, and thus separated from time segments only comprising other sound sources (e.g. artificially generated noise). In an embodiment, the voice detector is adapted to detect as a VOICE also the user's own voice. Alternatively, the voice detector is adapted to exclude a user's own voice from the detection of a VOICE.

In an embodiment, the hearing assistance device comprises an own voice detector for detecting whether a given input sound (e.g. a voice) originates from the voice of the user of the system. In an embodiment, the microphone system of the hearing assistance device is adapted to be able to differentiate between a user's own voice and another person's voice and possibly from NON-voice sounds.

In an embodiment, the hearing assistance device comprises an acoustic (and/or mechanical) feedback suppression system. Acoustic feedback occurs because the output loudspeaker signal from an audio system providing amplification of a signal picked up by a microphone is partly returned to the microphone via an acoustic coupling through the air or other media. The part of the loudspeaker signal returned to the microphone is then re-amplified by the system before it is re-presented at the loudspeaker, and again returned to the microphone. As this cycle continues, the effect of acoustic feedback becomes audible as artifacts or even worse, howling, when the system becomes unstable. The problem appears typically when the microphone and the loudspeaker are placed closely together, as e.g. in hearing aids or other audio systems. Some other classic situations with feedback problem are telephony, public address systems, headsets, audio conference systems, etc. Frequency dependent acoustic, electrical and mechanical feedback identification methods are commonly used in hearing assistance devices, in particular hearing instruments, to ensure their stability. Unstable systems due to acoustic feedback tend to significantly contaminate the desired audio input signal with narrow band frequency components, which are often perceived as howl or whistle. It has been proposed that the stability of a system may be increased by specifically altering its transfer function at critical frequencies [Ammitzboll, 1987]. This can, for example, be achieved with a narrow frequency specific stop-band filter, referred to as a notch-filter [Porayath, 1999]. The disadvantage of this method is that gain has to be sacrificed at and around critical frequencies. More advanced techniques suggest feedback cancellation by subtracting an estimate of the feedback signal within the hearing assistance device. It has been proposed to use a fixed coefficient linear time invariant filter for the feedback path estimate [Dyrlund, 1991]. This method proves to be effective if the feedback path is steady state and, therefore, does not alter over time. However, the feedback path of a hearing assistance device, e.g. a hearing aid, does vary over time and some kind of tracking ability is often preferred. Adaptive feedback cancellation has the ability to track feedback path changes over time. It is also based on a linear time invariant filter to estimate the feedback path but its filter weights are updated over time [Engebretson, 1993]. The filter update may be calculated using stochastic gradient algorithms, including some form of the popular Least Mean Square (LMS) or the Normalized LMS (NLMS) algorithms. They both have the property to minimize the error signal in the mean square sense with the NLMS additionally normalizing the filter update with respect to the squared Euclidean norm of some reference signal. Various aspects of adaptive filters are e.g. described in [Haykin]. A more advanced method combines stochastic gradient algorithms with statistical evaluation of the AFC filter coefficients over time and employs control circuitry in order to ensure the filter coefficients to be updated adequately in noisy situations [Hansen, 1997]. The statistical evaluation is sensible to changes of the phase response and magnitude-frequency response of the feedback path. Traditionally, design and evaluation criteria such as mean-squared error, squared error deviation and variants of these are widely used in the design of adaptive systems.

In an embodiment, the hearing assistance device further comprises other relevant functionality for the application in question, e.g. compression, noise reduction, etc.

In an embodiment, the hearing assistance device comprises a listening device, e.g. a hearing aid, e.g. a hearing instrument, e.g. a hearing instrument adapted for being located at the ear or fully or partially in the ear canal of a user, e.g. a headset, an earphone, an ear protection device or a combination thereof.

In a further aspect, use of a hearing assistance device as described above, in the 'detailed description of embodiments' and in the claims, is moreover provided. In an embodiment, use is provided in a system comprising audio distribution, e.g. a system comprising a microphone and a loudspeaker in sufficiently close proximity of each other to cause feedback from the loudspeaker to the microphone during operation by a user. In an embodiment, use is provided in a system comprising one or more hearing instruments, headsets, ear phones, active ear protection systems, etc., e.g. in handsfree telephone systems, teleconferencing systems, public address systems, karaoke systems, classroom amplification systems, etc.

In a further aspect of the invention, the object is achieved by a method of performing eye monitoring of the angular orientation of the pupil as well as the size.

In a further aspect of the invention, the object is achieved by a method of controlling the hearing assistive device according to brain signals.

It is intended that some or all of the structural features of the device described above, in the 'detailed description of embodiments' or in the claims can be combined with embodiments of the method, when appropriately substituted by a corresponding process and vice versa. Embodiments of the method have the same advantages as the corresponding devices. Further, any feature, detail, structure and/or aspect may be combined individually or in their entirety with any other feature, detail, structure and/or aspect in the present specification.

In an aspect, a tangible computer-readable medium storing a computer program comprising program code means for causing a data processing system to perform at least some (such as a majority or all) of the steps of the method described above, in the 'detailed description of embodiments' and in the claims, when said computer program is executed on the data processing system is furthermore provided by the present application. In addition to being stored on a tangible medium such as diskettes, CD-ROM-, DVD-, or hard disk media, or any other machine readable medium, and used when read directly from such tangible media, the computer program can also be transmitted via a transmission medium such as a wired or wireless link or a network, e.g. the Internet, and loaded into a data processing system for being executed at a location different from that of the tangible medium.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

A Listening System:

In a further aspect, a listening system comprising a hearing assistance device as described above, in the 'detailed description of embodiments', and in the claims, AND an auxiliary device is moreover provided.

In an embodiment, the system is adapted to establish a communication link between the hearing assistance device and the auxiliary device to provide that information (e.g. control and status signals, possibly audio signals) can be exchanged or forwarded from one to the other.

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing assistance device. In an embodiment, the auxiliary device is or comprises a remote control for controlling functionality and operation of the hearing assistance device(s).

In an embodiment, the auxiliary device is another hearing assistance device. In an embodiment, the listening system comprises two hearing assistance devices adapted to implement a binaural listening system, e.g. a binaural hearing aid system.

Definitions:

In the present context, a 'hearing assistance device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears.

A 'hearing assistance device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing assistance device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing assistance device may comprise a single unit or several units communicating electronically with each other.

More generally, a hearing assistance device comprises an input transducer for receiving an acoustic signal from a user's surroundings and providing a corresponding input audio signal and/or a receiver for electronically (i.e. wired or wirelessly) receiving an input audio signal, a signal processing circuit for processing the input audio signal and an output means for providing an audible signal to the user in dependence on the processed audio signal. In some hearing assistance devices, an amplifier may constitute the signal processing circuit. In some hearing assistance devices, the output means may comprise an output transducer, such as e.g. a loudspeaker for providing an air-borne acoustic signal or a vibrator for providing a structure-borne or liquid-borne acoustic signal. In some hearing assistance devices, the output means may comprise one or more output electrodes for providing electric signals.

In some hearing assistance devices, the vibrator may be adapted to provide a structure-borne acoustic signal transcutaneously or percutaneously to the skull bone. In some hearing assistance devices, the vibrator may be implanted in the middle ear and/or in the inner ear. In some hearing assistance devices, the vibrator may be adapted to provide a structure-borne acoustic signal to a middle-ear bone and/or to the cochlea. In some hearing assistance devices, the vibrator may be adapted to provide a liquid-borne acoustic signal to the cochlear liquid, e.g. through the oval window. In some hearing assistance devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

A 'listening system' refers to a system comprising one or two hearing assistance devices, and a 'binaural listening system' refers to a system comprising one or two hearing assistance devices and being adapted to cooperatively provide audible signals to both of the user's ears. Listening systems or binaural listening systems may further comprise 'auxiliary devices', which communicate with the hearing assistance devices and affect and/or benefit from the function of the hearing assistance devices. Auxiliary devices may be e.g. remote controls, audio gateway devices, mobile phones, public-address systems, car audio systems or music players. Hearing assistance devices, listening systems or binaural listening systems may e.g. be used for compensating for a hearing-impaired person's loss of hearing capability, augmenting or protecting a normal-hearing person's hearing capability and/or conveying electronic audio signals to a person.

Further objects of the application are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which:

FIG. 6 shows a model for extraction of features of a power spectral within an alpha band, and FIG. 7A and FIG. 7B show two embodiments eye monitoring means for controlling for a hearing assistance device.

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

Figure 1A:
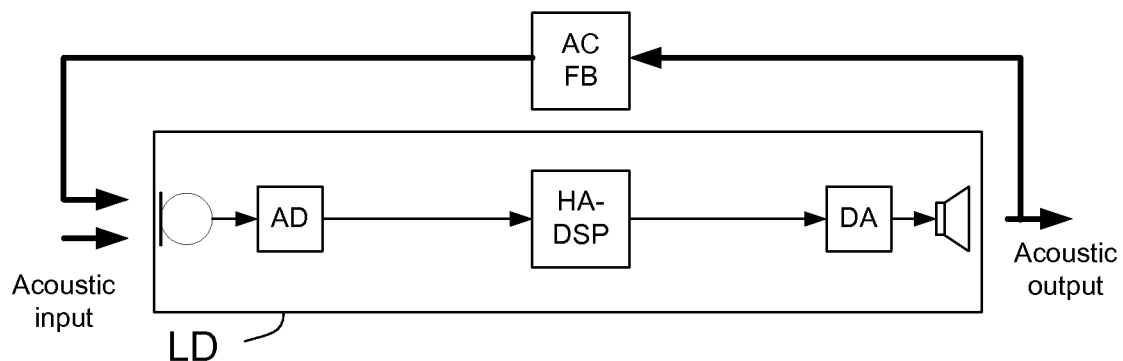
FIGS. 1A-1D show four embodiments of a hearing assistance device.
Figure 1B:
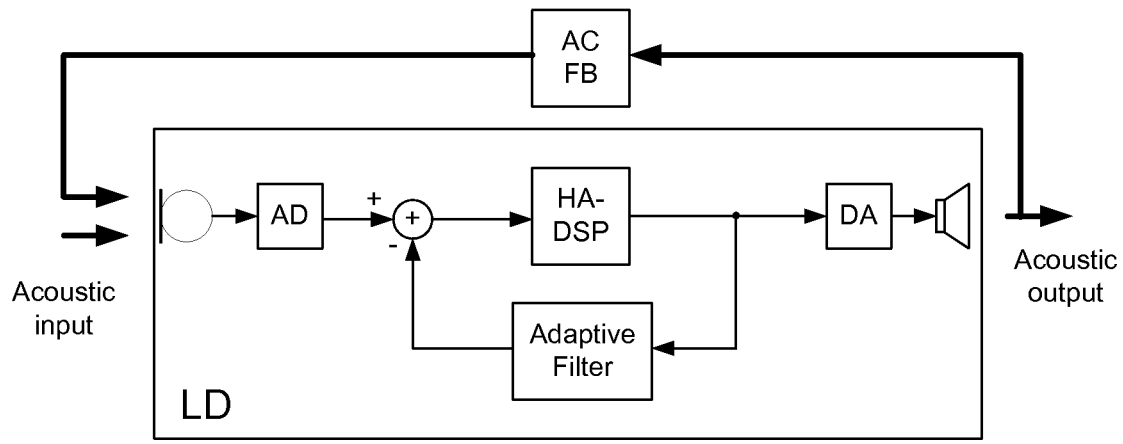
Figure 1C:
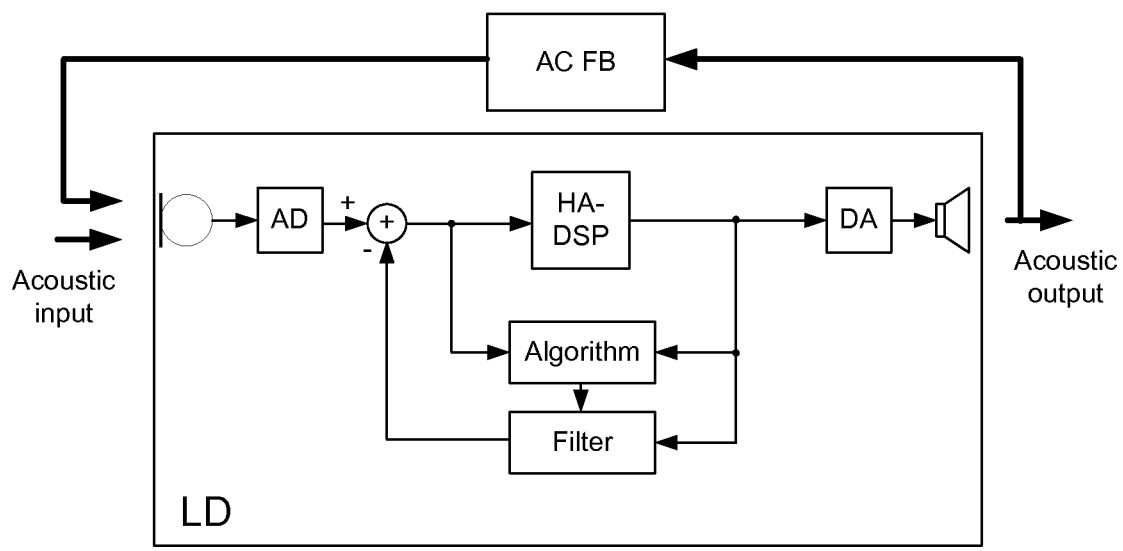
Figure 1D:
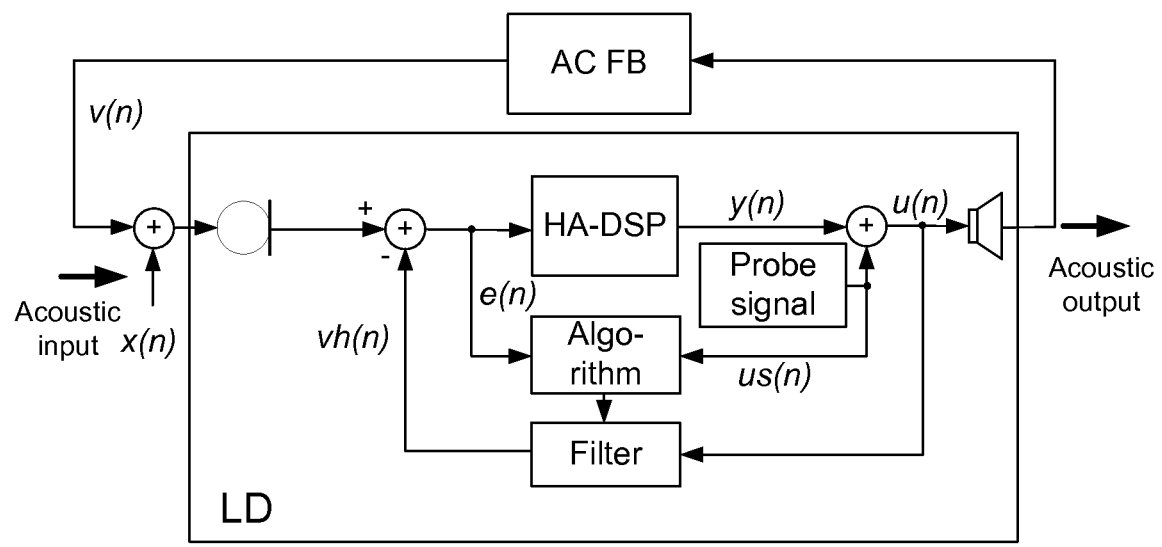

FIGS. 1A-1D show four embodiments of a hearing assistance device. FIG. 1A shows a simple hearing aid comprising a forward or signal path from an input transducer to an output transducer and a forward path being defined there between and comprising a processing unit HA-DSP for applying a frequency dependent gain to the signal picked up by the microphone and providing an enhanced signal to the output transducer. Hearing aid feedback cancellation systems (for reducing or cancelling acoustic feedback from an 'external' feedback path (AC FB) from output to input transducer of the hearing aid) may comprise an adaptive filter ('Adaptive filter' in FIG. 1B), which is controlled by a prediction error algorithm, e.g. an LMS (Least Means Squared) algorithm, in order to predict and cancel the part of the microphone signal that is caused by feedback (from the receiver of the hearing aid. FIGS. 1B and 1C illustrate examples of this. The adaptive filter (in FIG. 1C comprising a variable 'Filter' part end a prediction error or 'Algorithm' part) is (here) aimed at providing a good estimate of the 'external' feedback path from the digital-to-analogue (DA) to the analogue-to-digital (AD) converters. The prediction error algorithm uses a reference signal (e.g. the output signal) together with a signal originating from the microphone signal to find the setting of the adaptive filter that minimizes the prediction error when the reference signal is applied to the adaptive filter. The forward path of the hearing aid comprises signal processing ('HA-DSP' in FIG. 1) e.g. adapted to adjust the signal to the impaired hearing of a user. The estimate of the feedback path provided by the adaptive filter is (FIGS. 1B and 1C) subtracted from the microphone signal in sum unit '+' providing a so-called 'error signal' (or feedback-corrected signal), which is fed to the processing unit HA-DSP and to the algorithm part of the adaptive filter (FIG. 1C). To provide an improved decorrelation between the output and input signal, it may be desirable to add a probe signal to the output signal. This probe signal can be used as the reference signal to the algorithm part of the adaptive filter, as shown in FIG. 1D (output of block 'Probe signal' in FIG. 1D), and/or it may be mixed with the ordinary output of the hearing aid to form the reference signal.

Figure 2:
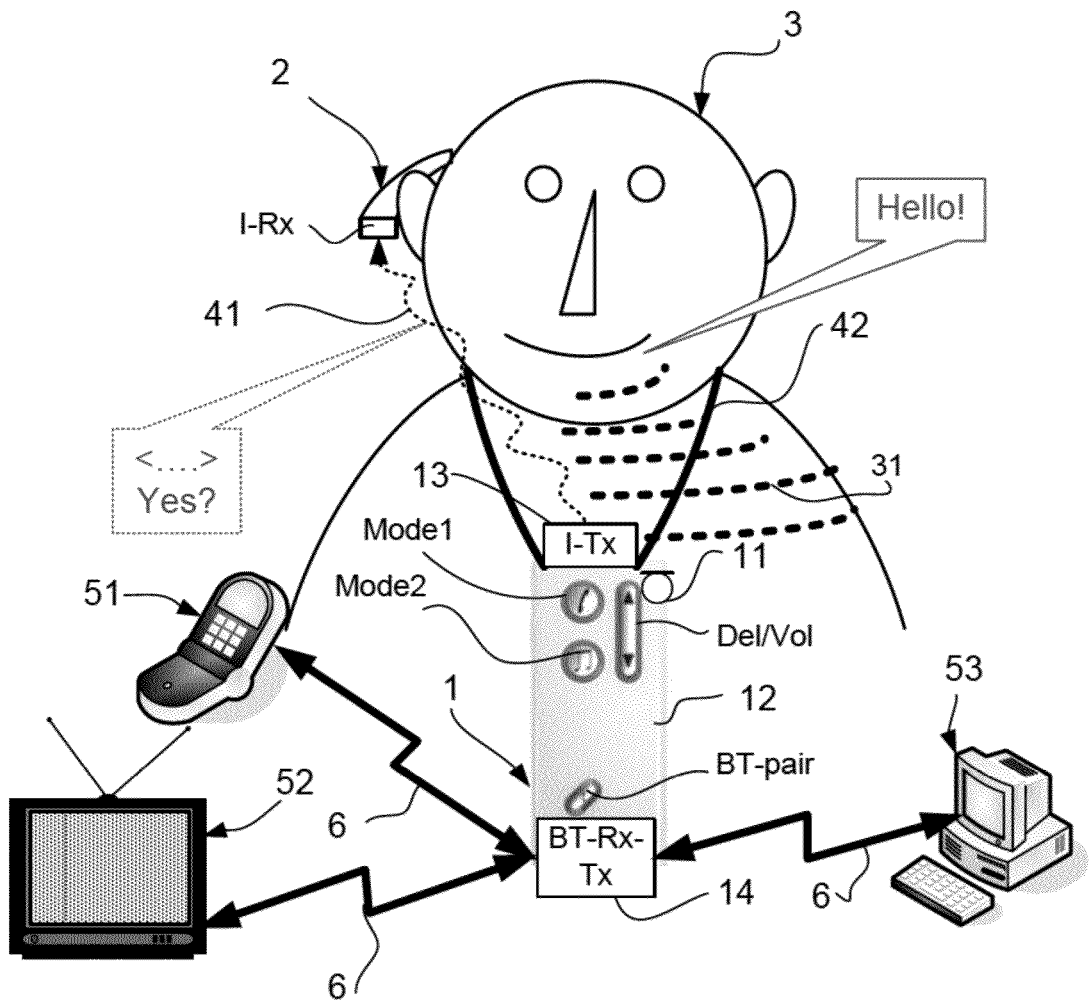
FIG. 2 shows an embodiment of a listening system comprising a hearing assistance device and an audio gateway, the system being adapted for establishing a communication link between the two devices.

FIG. 2 shows an embodiment of a listening system comprising a hearing assistance device and an audio gateway, the system being adapted for establishing a communication link between the two devices. FIG. 2 shows an application scenario of an embodiment of a portable listening system according to the present invention, wherein the audio gateway device 1 comprises an audio selection device adapted for receiving a multitude of audio signals (here shown from an entertainment device, e.g. a TV 52, a telephone apparatus, e.g. a mobile telephone 51, a computer, e.g. a PC 53, and an external microphone xMIC for picking up sounds xIS from the environment, e.g. the voice of another person). In the embodiment of FIG. 2, the microphone 11 of the audio gateway device is adapted for picking up the user's own voice 31 and capable of being connected to one or more of the external audio sources 51, 52, 53 via wireless links 6, here in the form of digital transmission links according to the Bluetooth standard as indicated by the Bluetooth transceiver 14 (BT-Tx-Rx) in the audio gateway device 1. The audio sources and the audio gateway device may be paired using the button BT-pair. Once paired, the BT-address of the audio source may be stored in a memory of the audio gateway device for easy future pairing. The links may alternatively be implemented in any other convenient wireless and/or wired manner, and according to any appropriate modulation type or transmission standard, possibly different for different audio sources. Other audio sources than the ones shown in FIG. 2 may be connectable to the audio gateway, e.g. an audio delivery device (such as a music player or the like). The audio gateway device 1 further comprises a selector/combiner unit (not shown in FIG. 2) adapted for selecting and/or combining an appropriate signal or combination of signals for transmission to the hearing assistance device 2. The intended mode of operation of the listening system can be selected by the user via mode selection buttons Mode1 and Mode2. Here Mode1 indicates e.g. a telephone conversation mode (where the audio signal from a currently actively paired mobile telephone is selected) and Mode2 indicates e.g. an entertainment device mode (where the audio signal from a currently actively paired entertainment device, e.g. the TV or a music player, is selected). The particular selected mode determines the signals to be selected/combined in the selector/combiner unit for transmission to the hearing assistance device. In Mode1, the incoming signal from the mobile telephone is transmitted to the hearing assistance device (optionally combined with an own voice signal picked up by microphone 11). In Mode2, the audio signal from an entertainment device is selected and transmitted to the hearing assistance device. The audio gateway device may further have the function of a remote control of the hearing assistance device, e.g. for changing program or operating parameters (e.g. volume, cf. Vol-button) in the hearing assistance device.

The hearing assistance device 2 is shown as a device mounted at the ear of a user 3. The hearing assistance device 2 of the embodiment of FIG. 2 comprises a wireless transceiver, here indicated to be based on inductive communication (I-Rx). The transceiver (at least) comprises an inductive receiver (i.e. an inductive coil, which is inductively coupled to a corresponding coil in a transceiver (I-Tx) of the audio gateway device 1), which is adapted to receive the audio signal from the audio gateway device (either as a baseband signal or as a modulated (analogue or digital) signal, and in the latter case to extract the audio signal from the modulated signal). The inductive link 41 between the audio gateway device and the hearing assistance device is indicated to be one-way, but may alternatively be two-way (e.g. to be able to exchange control signals between transmitting 1 and receiving 2 device, e.g. to agree on an appropriate transmission channel). Alternatively or additionally, the hearing assistance device (and/or the audio gateway device) may be adapted to receive an audio signal from a telecoil (T-coil) in the environment of the device.

The audio gateway device 1 is shown to be carried around the neck of the user 3 in a neck-strap 42. The neck-strap 42 may have the combined function of a carrying strap and a loop antenna into which the audio signal from the audio gateway device is fed for better inductive coupling to the inductive transceiver of the hearing assistance device.

Figure 3:
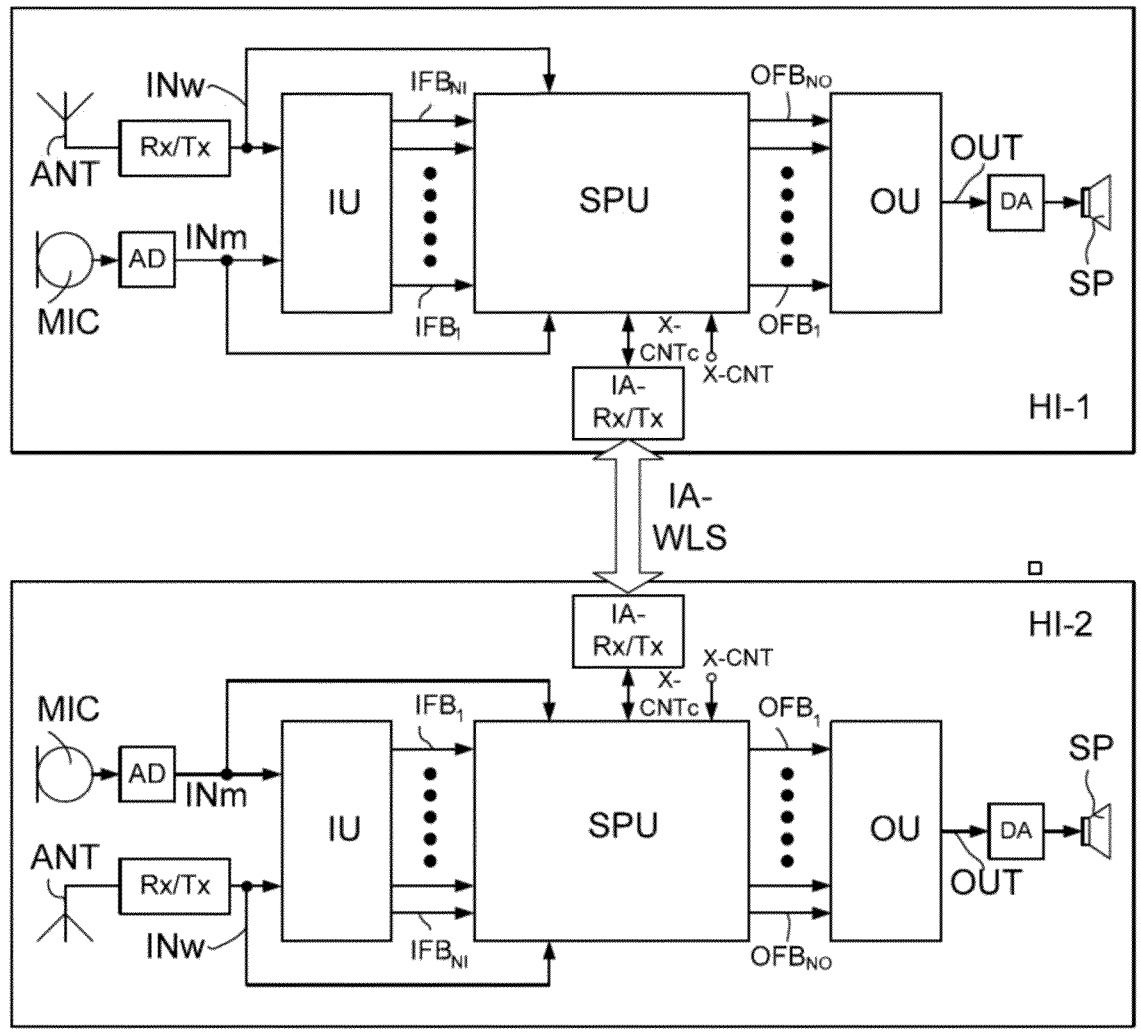
FIG. 3 shows an embodiment of a binaural hearing aid system comprising first and second hearing instruments.

FIG. 3 shows an embodiment of a binaural hearing system comprising first and second hearing instruments. The binaural hearing system comprises first and second hearing instruments (HI-1, HI-2) adapted for being located at or in left and right ears of a user. The hearing instruments are adapted for exchanging information between them via a wireless communication link, e.g. a specific inter-aural (IA) wireless link (IA-WLS). The two hearing instruments HI-1, HI-2 are adapted to allow the exchange of status signals, e.g. including the transmission of characteristics of the input signal received by a device at a particular ear to the device at the other ear. To establish the inter-aural link, each hearing instrument comprises antenna and transceiver circuitry (here indicated by block IA-Rx/Tx). Each hearing instrument HI-1 and HI-2 is an embodiment of a hearing assistance devise as described in the present application, here as described in connection with FIG. 8. In the binaural hearing system of FIG. 3, a control signal X-CNTc generated by a control part of the control and processing unit (SPU) of one of the hearing instruments (e.g.

HI-1) is transmitted to the other hearing instrument (e.g. HI-2) and/or vice versa. The control signals from the local and the opposite device are e.g. used together to influence a decision or a parameter setting in the local device. The control signals may e.g. comprise information that enhances system quality to a user, e.g. improve signal processing. The control signals may e.g. comprise directional information or information relating to a classification of the current acoustic environment of the user wearing the hearing instruments, etc. In an embodiment, the listening system further comprises an audio gateway device for receiving a number of audio signals and for transmitting at least one of the received audio signals to the hearing assistance devices (e.g. hearing instruments). In an embodiment, the listening system is adapted to provide that a telephone input signal can be received in the hearing assistance device(s) via the audio gateway.

A brain-computer interface (BCI) is a communication system that can help users interact with the outside environment by translating brain signals into machine commands. The use of electroencephalographic (EEG) signals has become the most common approach for a BCI because of their usability and strong reliability. Many EEG-based BCI devices have been developed with traditional wet- or micro-electro-mechanical-system (MEMS)-type EEG sensors. However, those traditional sensors have uncomfortable disadvantage and require conductive gel and skin preparation on the part of the user. Therefore, acquiring the EEG signals in a comfortable and convenient manner is an important factor that should be incorporated into a novel BCI device.

Brain Computer Interfaces to control a mouse on a screen are being developed. From MIT Technology Review May 16, 2013: Roozbeh Jafari, at the University of Texas and Samsung researchers working with a Brain Computer Interface (BCI) to test how people can use their thoughts to launch an application, select a contact, select a song from a playlist, or power up or down a Samsung Galaxy Note 10.1. Such a system could be described as a system sensitive to space gestures. While Samsung has no immediate plans to offer a brain-controlled phone, the early-stage research, which involves a cap studded with EEG-monitoring electrodes, shows how a brain-computer interface could help people with mobility issues complete tasks that would otherwise be impossible. Brain-computer interfaces that monitor brainwaves through EEG have already made their way to the market. NeuroSky's headset uses EEG readings as well as electromyography to pick up signals about a person's level of concentration to control toys and. Emotiv Systems has a headset that reads EEG and facial expression to enhance the experience of gaming. To use EEG-detected brain signals to control a smartphone, the Samsung and UT Dallas researchers monitored well-known brain activity patterns that occur when people are shown repetitive visual patterns. In their demonstration, the researchers found that people could launch an application and make selections. Jafari's research is addressing another challenge—developing more convenient EEG sensors. Classic EEG systems have gel or wet contact electrodes, which means a bit of liquid material has to come between a person's scalp and the sensor.

"Depending on how many electrodes you have, this can take up to 45 minutes to set up, and the system is uncomfortable," says Jafari. His sensors, however, do not require a liquid bridge and take about 10 seconds to set up, he says.

But they still require the user to wear a cap covered with wires. The concept of a dry EEG is not new, and it can carry the drawback of lower signal quality, but Jafari says his group is improving the system's processing of brain signals. Ultimately, if reliable EEG contacts were convenient to use and slimmed down, a brain-controlled device could look like "a cap that people wear all day long," says Jafari.

Manual or automatic control of Hearing aid parameters (to invoke directionality, noise reduction, change volume, change program etc) are today either made by button presses either though buttons on the hearing aid/streamer/smartphone or automatically invoked based on algorithms that take use patterns or environmental patterns into account.

The following problems are identified based on the prior art:
(1) Automatic control of hearing aid parameters does not account for the intent of the user. The only way to get user intent is through manual button presses.
(2) Brain Computer Interfaces are large and requires either an EEG hat, headband or similar to host the EEG electrodes. This makes the equipment vulnerable to electrode movements and limits the measure precision from the equipment, since the electrodes are not fixated. This also requires re-calibration each time the equipment is removed.

Figure 4:
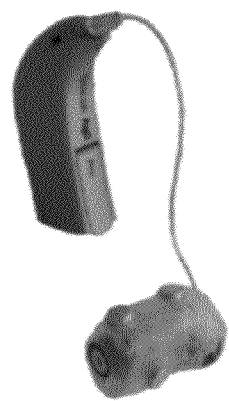
FIG. 4 shows a first embodiment of a hearing assistance device comprising a brain interface means.
Figure 5:
FIG. 5 shows a second embodiment of hearing assistance device comprising brain interface means.

FIGS. 4 and 5 respectively show a first and second embodiment of the invention, which solves the above identified problem by having either monaural or binaural ear EEG electrodes inserted to the ear canal. The Ear Electrodes picks up the intended space gestures, e.g. think of a space to the left of you to control e.g. the directionality pattern of a beamformer, and appropriate algorithms.

The invention solves the fixation and calibration problem by making individualized earmoulds (FIG. 5) that contains ear EEG electrodes (the blue pads) which ensure that insertion and re-insertion puts the electrodes in almost the exact place.

One embodiment of the invention takes monaural (or binaural) ear EEG signals. To amplify and filter the EEG signals, a pre-amplifier, a band-pass filter (0.5~50 Hz) and an analog-to-digital converter (ADC) are embedded into a circuit board as a bio-signal amplifier and acquisition component modules. The gain of the amplifier and acquisition component can be set to approximately 5500. An ADC with 12-bit resolution can be used to digitize the EEG signals, with a sampling rate of 256 Hz for the amplified and filtered EEG signals. In the microprocessor component, the EEG signals are probed using an ADC were digitally stored. A moving average filter with the frequency at 50 Hz or 60 Hz was then applied to reject any power-line interference.

One example of an algorithm is presented by Lun-De Liao et al, 2012. To change the hearing aid parameters the user should be trained intend to make the hearing aid change according to the following.

The users have to make a moving gesture—e.g. to move a directional microphone target to the left or right thinking of the target direction; they then obtain a score based on the distance between the achieved direction on the target and the center of the target. In the training session there can be a screen that indicates a bar on the screen. There can be a bar on the right of the screen, a target at the center of the screen, and a score at the top right of the screen. The bar indicate the focusing level (FL) of this user during the steering of the directional microphone. In other words, the FL value was the main controller. If the value of the FL is high, then the target directionality is close to the center of the target, and then the score will be high. If the value of the FL was low, the targeting of the directionality was far from the center of the target and resulted in a lower score. The user's task will be to make the FL value as high as possible by trying to focus the directionality to the center of the target To measure the FL values of the users, a simple, real-time, mental focusing level detection algorithm for gaming control can be used. The flowchart of this FL detection algorithm is shown in the FIG. 6. The FL detection algorithm includes three major steps: 1) rejection of the artifact signals, 2) extraction of the focusing feature and 3) determination of the FL values. First, preprocessing of the original EEG signals will be performed to reject the noise signals. It is well known that the mentally focused state is highly associated with the alpha rhythm (8~12 Hz) of an EEG, and the noise artifacts were located in frequency regions that were different from the alpha rhythm frequency range. Accordingly, to reject the artifacts, a fast Fourier Transform was performed to obtain the EEG power spectrum patterns of the signals, and signals within the alpha band were retained.

Secondly, extraction of the focus feature was performed on the power spectrum within the alpha band. Previous studies have shown that the power of the alpha rhythm of an EEG grows as the user's mental state changes from focused to unfocused cognitive states. Therefore, the alpha band is the main frequency band that we used to indicate the user's focused state in the present study, and the 8~12 Hz frequency band of the original EEG signals was selected for the FL detection algorithm. The Focus Feature (FF) is defined as the inverse of the average power in the alpha rhythm, as shown in equations (1-3):

$$X = [X_1 \; X_2 \; X_3 \; ... \; X_{511} \; X_{512}] \quad (1)$$
$$Y = [Y_1 \; Y_2 \; Y_3 \; ... \; Y_{255} \; Y_{256}]$$
$$Y = FFT(X)$$

$$P_\alpha = \frac{1}{5} \sum_{n=8}^{12} Y_n \quad (2)$$

$$FF = PR_\alpha = 1/P_\alpha \quad (3)$$

X indicates the recorded samples in 2-s, where Xn is the nth sample. Y is the power spectrum of X, which is calculated by the FFT; Yn indicates the power in the nth rhythm.

The average power within the alpha band Pα is obtained by averaging the value of Y in the range from 8 to 12 Hz. PRα is the inverse of this average power in the alpha rhythm. The FF value is assumed to be equal to PRα. The power of the alpha rhythm has a negative relationship with the value of the FF. If the user is not focused, the power of the alpha rhythm will increase, and the value of the FF will decrease.

Lastly, a comparison of the user's current FF value with that at baseline was used to confirm whether or not the user was in a focused state and then to determine the FL based on the user's focused state. We assumed based on user feedback that the user was in a focused state in the beginning (baseline) and defined the user's FF at baseline as the baseline FF (BFF), which is the average of the FFs within the initial ten seconds. After we determined the BFF, the FF values were calculated every 2 s and were compared to the BFF. If the current FF value was higher than the BFF value, the user was considered to be in the focused state. If the current FF value was lower than the BFF value, the user was considered to be in the unfocused state. Finally, the values of the FL variation were determined according to the user's mental focus state. If the user was focused, the FL increased and vice-versa.

FIGS. 7A and 7B show a hearing device control using eye tracking and wearable camera.

The problem to be solved by this embodiment is that hearing devices cannot see what the wearer sees and cannot sense what the wearer is attending to. It is possible to correlate EEG signals with the sound signal to assess which signal the wearer is attending to. The EEG signals also provide insights into how much the current tasks load the wearer. However, is the same information available from other devices without the need for correlation between sound input and brain wave signals?

In many situations the wearer's attention can be estimated from inferring what the wearer is looking at. For hearing impaired listeners that additionally rely on lip reading this is certainly true. Thus the somewhat complicated task of correlating input sound and EEG signals can be replaced by eye tracking.

Additionally, eye tracking also enable an alternative way of measuring the cognitive load and the cognitive fitness (reciprocal of fatigue) by monitoring the pupil size and pupil reaction time.

The solution is combination of the functionality of at least one eye tracking device, at least one camera, and at least one hearing device. The combination can be achieved as a single device or as separate devices that communicate together.

Moreover, this allows the overall device to measure when the individual parameters of the hearing device have become outdated with respect to the wearer.

For smaller adjustments of the parameters, the device may try new parameter settings and monitor the benefit of those new parameter settings by comparing the cognitive load measures with the objective measures of the sound environment for several parameter configurations.

Wearable eye tracking may be an alternative to EEG for measuring cognitive function. Moreover when it is combined with the functionality of wearable cameras and infrared sensors (see FIG. 1) it provides information about what the wearer hears (the sound), sees (the picture), where the focus is (where the eyes point), how hard the listener is working to understand the scene (puppilomtry). This opens up for a novel use and operation of hearing devices.

The continuous measurement of the cognitive function of the wearer via pupilometry (i.e. determining angular orientation and size of pupil of an eye) allows the hearing aid to adapt to the cognitive load of the wearer such that processing adapts to the cognitive capacity (eGo processing). European patent application no.: EP12190377.7, which is incorporated herein by reference, describes hearing device with brain-wave dependent audio processing provides an example of monitoring the fit of the hearing device.

The continuous measurement of cognitive function along with the objective measures of the sound environment allows the device to monitor when the cognitive load is increasing in all sound environments. This may indicate that an adjustment of the hearing device is necessary.

This is achieved change detection on the relation between sound environment parameters and cognitive function.

The hearing device can make small adjustments to parameters in specific algorithms and monitor impact on the cognitive load in comparable sound environments to adapt the parameters of the hearing device to the user. This allows the hearing device to become more individualized as well as adjust to changes in the wearer needs.

As a diagnostic device it may operate without the functionality of the hearing device. Instead it measures the cognitive load of the wearer in certain controlled or ordinary environments and group the wearers hearing capabilities by comparing the cognitive load to objective measures of the sound environment with databases of such. This allows for screening and for more specific characterisation of the hearing capabilities of the wearer.

A further embodiment of the invention is a bone-conduction implant with EEG electrodes. It is known to control a hearing device in dependence on EEG signals measured on the user of the hearing aid. For instance, a hearing device may be fitted using hearing thresholds derived from EEG measurements. A hearing device having physical contact to the user's skin may have electrodes on its outside, which enables it to perform the EEG measurement without the use of external equipment.

The problem with the prior art is that bone-anchored hearing devices do typically not have contact with the user's skin and therefore cannot benefit from such a solution.

The solution is to place the EEG electrodes in the implant and let the hearing device connect to the EEG electrodes through conductive paths on or in the implant. The EEG electrodes may both be arranged in the portion of the implant which is located deep in the skull bone or one or both may be arranged nearer to the outer side of the skull bone.

The EEG electrodes may be arranged on the outside of the implant similar to what is disclosed in patent EP1843138B1. A number of processes exist to apply non-conductive and conductive paths and layers to metal objects, such as an implant. The hearing device may have a set of contacts arranged to connect to corresponding contacts on the implant when it is mechanically connected to the implant (or abutment).

A further embodiment of the invention is use of a measured EEG signal to distinguish between own voice and other sounds. It is known that EEG can be used for speaker recognition, i.e. by correlating sound signals and EEG signals, it can be determined from the EEG signals who the person is listening to.

It is likely that it also could be determined from the EEG signals if the person himself is talking, i.e. use EEG for own voice detection. The idea is that different parts of the brain are when a person is talking and when a person is listening, and therefore it may be possible to distinguish own voice from other people talking.

A further embodiment of the invention is a hearing device with EEG-based feedback cancellation.

Hearing devices tend to produce howls and other artefacts when the acoustic gain is high. Various methods to suppress such artefacts are known in the art. In many of these methods, it remains a challenge to distinguish between artefacts and howl-like sounds from the environment.

Since artefacts generally deteriorate the sound quality and thus cause irritation to the user, EEG signals measured on the user probably show some indication whether a howl currently being heard is an artefact or a wanted signal, such as e.g. a flute note in a concert.

The solution is therefore to use EEG signals to assist the already available feedback cancellation system in deciding whether a howl-like sound should be attenuated or not.

The hearing device preferably has electrodes on the outside of its housing and thus measures EEG signal. When a howl is detected in the feedback cancelling system, the EEG signals are evaluated to determine whether the user is annoyed with the howl or not, and if the user is annoyed, the howl is attenuated.

A further embodiment of the invention is an ear-level listening device with EEG-controlled music selection Many people listen to music via an ear-level listening device, such as an earphone connected to a music player, smartphone or the like. Wearers of hearing aids may listen to music using their hearing devices essentially as earphones. Listening to music from a limited music collection does not provide satisfactory variation in the music. On the other hand, searching for and retrieving new music, e.g. via the internet, disturbs the relaxation or invigoration experienced by the music listening.

Since a hearing device, such as a hearing aid or an earphone, could be provided with EEG electrodes for other purposes, the EEG signals could also be used to determine how much the wearer likes the music presently being played. By analysing features of liked and non-liked music, the hearing device could then predict features of likable music and search available music resources—such as the internet—for random music having such features and add found music to the collection.

Several studies were made that indicate that there is a correlation between listened-to music and EEG signals. Also, algorithms are known that suggest new music based on previously played (and supposedly liked) music. These could be combined in a hearing device provided with EEG electrodes, in a binaural system comprising such hearing devices, and/or in a smartphone connected to such hearing device(s).

A further aspect of the present disclosure deals with hearing instrument with implantable EEG electrode. The use of EEG electrodes is discussed in other parts of the present disclosure, which may be combined with any part of this aspect in whole or in parts.

Establishing good contact with skin for an EEG electrode embodied in an In-The-Ear or Behind-The-Ear hearing instrument is challenging. Moreover it is also challenging to achieve sufficient distance between the electrodes. Therefore it is an advantage to improve signal reception, as signals received by an EEG electrode may be weak and/or noise filled. Thus, an implantable hearing instrument is advantageously connected or connectable to one or more EEG electrodes that may be positioned under the skin at positions where they will be able to achieve appropriate signal conditions.

For a bone-anchored hearing instrument, there could be a number of electrodes connected to a titanium anchor of the bone-anchored instrument, which may then be positioned in a star shape around the titanium anchor in the implanted state. Similar positions for a cochlear implant could be envisioned, with approximately similar location/distribution as in the case of a titanium anchor.

For implantable hearing instruments and middle ear prostheses, the electrodes are best placed or positioned on the ear canal surface near the implantable instrument or prosthesis and around the microphone in a configuration similar to the titanium anchor or cochlear implant case above.

This part of the present disclosure may be characterised by the following items:

1. A hearing instrument connectable to an implantable EEG electrode, wherein the implantable EEG electrode is configured to be placed under the skin at the head of a user.

2. The hearing instrument according to item 1, wherein the hearing instrument is a bone anchored instrument or cochlear implant.

3. The hearing instrument according to item 1 or 2, wherein a plurality of implantable EEG electrodes are connected to the hearing instrument.

4. The hearing instrument according to item 2 or 3, wherein one or more of the EEG electrodes are connected to a titanium anchor of the bone anchored instrument.

5. The hearing instrument according to item 2 or 3, wherein one or more of the EEG electrodes are connected to a lead of a cochlear implant.

6. The hearing instrument according to any one of items 2-4, wherein one or more of the EEG electrodes are configured to be arranged in a star-pattern around the hearing instrument in an implanted state.

7. The hearing instrument according to any one of items 1-6, wherein the EEG electrode or EEG electrodes are configured to be placed at the ear canal surface near the implantable instrument or prosthesis.

In a still further aspect the present disclosure presents eye-movement tracking from in-ear devices.

Observation of a person's eyes can be used to provide information about the cognitive state of the person, and also provides a means for the person to control external devices. Examples of the former are frequency and duration of eye blinks, which can be used to indicate cognitive load, fatigue or sleepiness (e.g. Caffier et al 2003). Examples of the latter are direction and change of direction of gaze, which can be used to interact with and control electronic devices (e.g. Singh & Singh 2012).

Common techniques for recording eye blink and gaze activity include video-based eye-tracking (e.g. Bergasa et al 2006) and EOG (Electrooculography) (Singh & Singh 2012). The former technique requires video equipment, either stationary or body-mounted, the most compact example to date being mounted on an eyeglass-like device. The latter technique requires a plurality of electrodes in contact with the scalp. The most compact examples to date encompass light-weight skeleton headsets. None of the current solutions for recording eye activity enable cosmetically acceptable forms of device, thus limiting their application to artificial or highly constrained situations.

When measuring EEG, EOG is an unavoidable artifact arising from the electrical signals generated by the electrical potential differences between the back of the eyeball (the retina) and the front (the cornea). Due to the large negative potential of the optic nerve, exiting the eye at the retina, the eyeball forms a large electrical dipole generating changes in the electrical potentials when moved. Shifting gaze is associated with horizontal and vertical movement of the eyes. Also during eye blink, the eyeballs are turned upwards which, together with the muscle activity required to close and open the eyelids, generate very distinct patterns in the EEG, larger in magnitude than the brain EEG itself. Due to the large amplitude of the eye movements, these are often identified and removed using techniques such as independent component analysis, before analyzing the EEG. The same technique can instead be applied to extract the EOG from the EEG for further analysis of the eye movements.

Figure 8:
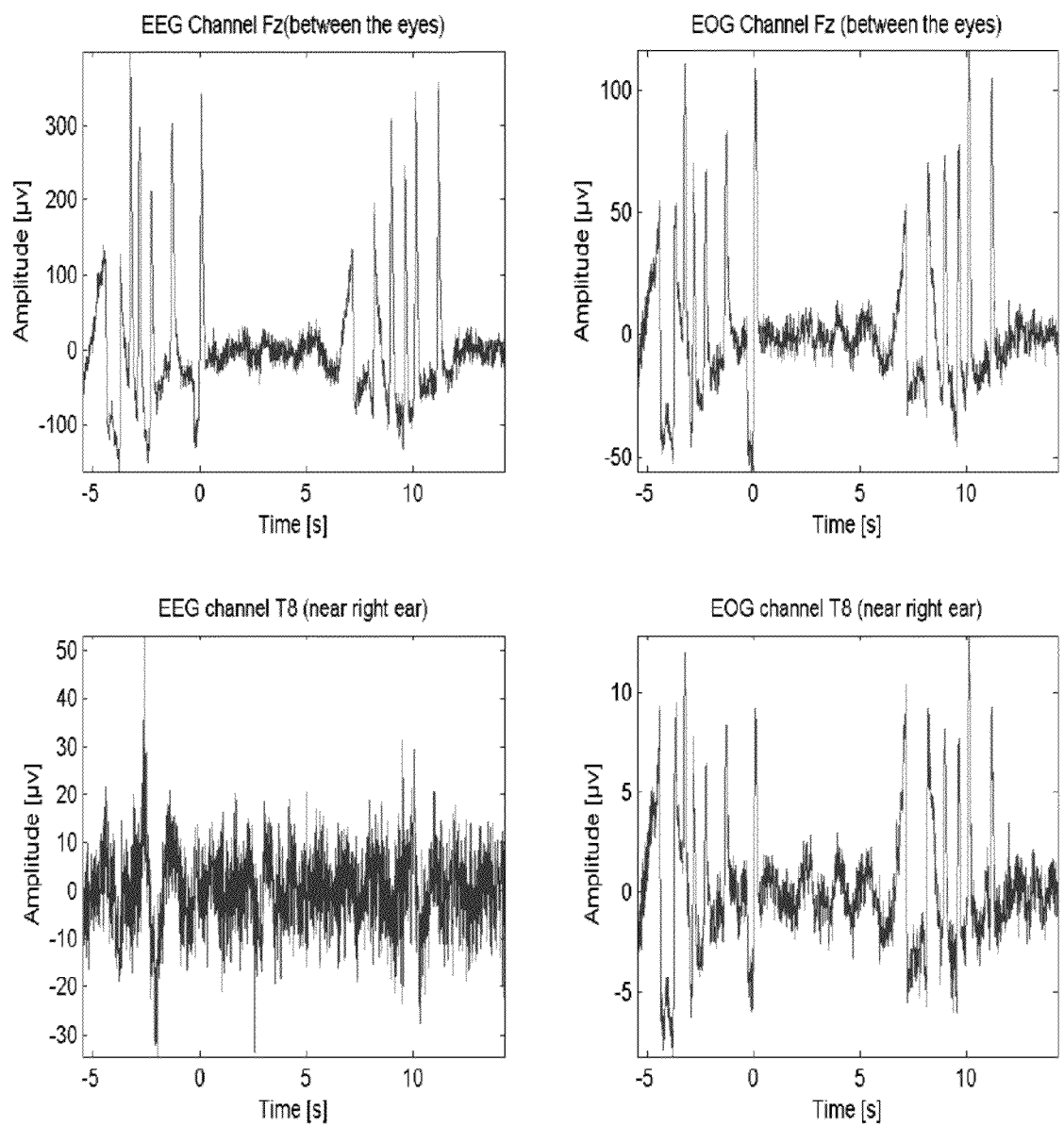
FIG. 8 illustrates an example of the EEG and the EOG that can be extracted from it, based on independent components analysis for an electrode position frontally, close to the eyes, and an electrode on the side of the head near the right ear.

It has been demonstrated that EEG signals of usable quality can be obtained from closely-spaced electrodes placed within the human outer ear canal. By combining this technology with signal processing algorithms in a small in-ear device, it is possible to detect eye activity such as blinks and changes of gaze direction. FIG. 8 illustrates an example of the EEG and the EOG that can be extracted from it, based on independent components analysis for an electrode position frontally, close to the eyes, and an electrode on the side of the head near the right ear. From FIG. 8 it is evident that it is possible to identify both blinks and gaze shifts based on the EEG near the right ear. Simple detection algorithms can be applied to detect the blinks, seen as large spikes of activity, and gaze shift, seen as intervals of baseline shifts, to compute features such as gaze and blink rate, direction, and duration.

Combining the EEG recording in-ear device with wireless data transmission to remote devices, actions can be initiated dependent on the detected state of blinking or eye movements, such as warnings of fatigue or control of arbitrary apparatus. With the addition of sound-producing components to the in-ear device, it becomes possible to make an unobtrusive, self-contained system capable of issuing warnings to the wearer when he/she is approaching or is in a state deserving of attention, such as a state of fatigue or drowsiness. Furthermore, if the device is a communication device such as a hearing aid, it becomes possible to control the behaviour of the device by deliberate blinking or gaze direction, or on the basis of the detected cognitive state.

The wearer's cognitive state could be distinguishable states categorised as: drowsy, alert, awake, sleeping, calm, stressed. Further or alternative categories may be envisioned. One or more threshold values or set or sets of threshold values may be used for determining which state the user is in.

Two Examples:

1. A communication device worn in or on the ear, which could be a hearing aid or a telephone headset. The device is equipped with EEG electrodes and includes eye-activity detection algorithms. This device could issue audible warning to the user in case of undesirable cognitive state (e.g. drowsiness) being detected, or change its mode of action dependent on the detected cognitive state, for example increase the degree of microphone directivity or noise reduction when cognitive load is high. Given wireless data transmission capabilities, it could relay information about the wearer's cognitive state to remote devices and people (work supervisors, care-givers etc.)

2. A communication device worn in or on the ear, such a device could be a hearing aid or a telephone headset. Equipped with EEG electrodes and including eye activity detection algorithms, this device could be controlled by deliberate patterns of eye-blinking by the user. For example, if devices are in both ears and there is communication between the two devices, blink the left eye to steer directional microphones to the left and vice versa.

Additionally, if the user is wearing such a device in both ears, communication of EEG signal parameters, preliminary decisions, or raw EEG signals between the two devices could be used to improve the accuracy and reliability of eye activity classification.

The EEG electrode or EEG electrodes may be positioned in or at an ear, e.g. in the ear canal or behind the ear, on the skin of the user, e.g. at an area of the skin behind the ear or near the temple, implanted under the skin, or any other suitable place depending on the type of EEG electrode used.

This part of the present disclosure may be characterized by the following items:

1. A communication device comprising an EEG electrode configured to receive electrical signals representing eye activity of a wearer, a processor configured for analysing the electrical signals representing eye activity so as to detect eye movement pattern, the processor further configured to operate the communication device based on the detected pattern.

2. The communication device according to item 1, further comprising a memory device storing a number of eye movement patterns and corresponding operation instructions, the processor configured to select from the number of operation instructions based on the detected pattern.

3. A communication device comprising an EEG electrode configured to receive electrical signals representing eye activity of a wearer, a processor configured for analysing the electrical signals representing eye activity so as to detect eye movement pattern, the processor configured to determine a cognitive state of a user based on the detected eye movement pattern, an alarm device in communication with the processor, the processor configured to operate the alarm in response the determined cognitive state.

4. The communication device according to item 3, wherein the cognitive states are classified as: deserving of attention or not deserving of attention, and the processor is configured to operate the alarm device when a shift from not deserving of attention state to a deserving of attention state is detected.

5. A method of operating a communication device comprising an EEG electrode configured to receive electrical signals representing eye activity of a wearer and a processor, the method comprising:
 processing signals from the EEG electrode to classify eye activity,
 determining, using the processor, if changes to the operating state of the communication device is required based on the classification of eye activity, operating the communication device accordingly.

6. The method according to item 5, wherein the communication device further comprises an alarm device, and the method further comprises:
 provided the classification of the eye activity results in determination of a state being classified as deserving of attention, operating the alarm device accordingly.

7. The method according to item 5, wherein the communication device comprises a directional microphone system having adaptable directionality, the method comprises:
 operating the directional microphone system based on the classification of the eye activity.

8. The method according to item 7, wherein the classification of the eye movement includes classifying eye movement as left and/or right shift in directionality of directional microphone system.

These and other items may be combined with any features mentioned through out the present disclosure.

Some preferred embodiments have been shown in the foregoing, but it should be stressed that the invention is not limited to these, but may be embodied in other ways within the subject-matter defined in the following claims and equivalents thereof. In addition, the embodiments of the invention may be combined together to form a wide variety of hearing assistance devices.

References

[Schaub; 2008] Arthur Schaub, Digital hearing Aids, Thieme Medical. Pub., 2008.

[Haykin] S. Haykin, Adaptive filter theory (Fourth Edition), Prentice Hall, 2001.

[Ammitzboll, 1987] U.S. Pat. No. 4,689,818, "Resonant peak control", 1987

[Porayath, 1999] U.S. Pat. No. 5,999,631 "Acoustic feedback elimination using adaptive notch filter algorithm", 1999

[Dyrlund, 1991] 0. Dyrlund, N. Bisgaard, "Acoustic feedback margin improvements in hearing instruments using a prototype DFS (digital feedback suppression) system", Scand Audiol, 20(1), pp. 49-53, 1991

[Engebretson, 1993] A. Engebretson, M. French-St. George, "Properties of an adaptive feedback equalization algorithm", J Rehabil Res Dev, 30(1), pp. 8-16, 1993

[Hansen, 1997] U.S. Pat. No. 5,680,467, "Hearing Aid Compensating for Acoustic Feedback", 1997

Lun-De Liao et al. (2012). Gaming control using a wearable and wireless EEG-based brain-computer interface device with novel dry foam-based sensors. Journal of NeuroEngineering and Rehabilitation 2012, 9:5 doi: 10.1186/1743-0003-9-5

Bergasa L M, Nuevo J, Sotelo M A, Barea R, Lopez M E (2006). Real-Time System for Monitoring Driver Vigilance. IEEE Transactions on Intelligent Transportation Systems 7(1): 63-77.

Caffier PP, Erdmann U, Ullsperger P (2003). Experimental evaluation of eye-blink parameters as a drowsiness measure. Eur J Appl Physiol 89: 319-325.

Singh H, Singh J (2012). A review on electrooculography. International Journal of Advanced Engineering Technology 3(4): 115-122.

The invention claimed is:

1. A communication device, comprising:
 an input for receiving a sound signal to be processed and presented to a user, and an output for outputting a signal to the user perceivable as sound;
 a processor for processing the sound signal in dependence of a setting or a set of settings to compensate a hearing loss profile; and
 a bio-signal acquisition and amplifier component in communication with the processor for providing the bio-signals as input to the processor, the processor controlling the setting or set of setting for operation of the communication device, wherein the bio-signal amplifier and acquisition component includes a wearable camera for eye-tracking.

2. The communication system according to claim 1, wherein the bio-signal amplifier and acquisition component comprises an ear EEG electrode which is comprised in a mould configured specifically for the user's ear canal.

3. The communication system according to claim 1, wherein the bio-signal amplifier and acquisition component comprises an ear EEG electrode configured to be inserted into an ear canal or on a skin-part of the head of a wearer or an implantable EEG electrode configured to be placed under the skin at the head and/or skull of the wearer or an implantable EEG electrode configured to be placed on the ear canal.

4. The communication system according to claim 1, wherein the bio-signal acquisition and amplifier component picks up intended space gestures.

5. The communication system according to claim 1, wherein the bio-signal represents eye movement and/or brain activity signals.

6. The communication system according to claim 1, comprising:
 an alarm device configured to provide an alarm signal if the signal from the bio-signal acquisition and amplifier component is determined to represent a cognitive state classified as a deserving of attention state.

7. A communication system comprising two communication devices according to claim 1, wherein each communication device is configured to be placed behind or at an ear of a wearer and each communication device comprising a brain-computer interface comprising an ear EEG electrode configured to be inserted in a respective ear canal of the wearer.

8. A method of controlling a communication device that includes an input for receiving a sound signal to be processed and presented to a user, an output for outputting a signal to a user perceivable as sound, a processor for processing the sound signal in dependence of a setting or a set of settings to compensate a hearing loss profile, and a bio-signal acquisition and amplifier component that includes a wearable camera for eye-tracking in communication with the processor for providing the bio-signals as input to the processor, the processor controlling the setting or set of settings for operation of the communication device, the method comprising:
 obtaining via bio-signal acquisition and amplifier component a bio-signal representing a gesture;

analysing the bio-signal for recognising an intended space gesture; and processing the intended space gesture to translate it to an input for the processor, wherein the wearable camera is directed at the eye of the user, and the gesture signal is determined via the wearable camera.

9. The method according to claim 8, wherein the user thinks of a target direction and using the target direction as input for the processor.

10. The method according to claim 8, wherein the user moves a limb in a target direction and using the target direction as input for the processor or wherein a user moves one or both eyes in the target direction and using the target direction as input for the processor.

11. The method according to claim 8, wherein the user imagines moving a limb in a target direction using the target direction as input for the processor or wherein the user imagines moving one or both eyes in a target direction and using the target direction as input for the processor.

12. The method according to claim 8, wherein the processing of the bio-signal translates to control of directionality pattern of a microphone beamformer in an intended direction or wherein the processing of the bio-signal translates to change of current program for sound processing, the method comprising operating the communication device accordingly.

13. The method according to claim 9, wherein a fatigue level is determined via the camera based on images of the pupil of the eye, by determining an angular orientation of the pupil and/or a size of the pupil.

14. The communication system according to claim 2, wherein the EEG electrode picks up intended space gestures.

15. The communication system according to claim 3, wherein the EEG electrode picks up intended space gestures.

16. The communication system according to claim 2, wherein the bio-signal represents eye movement and/or brain activity signals.

17. The communication system according to claim 3, wherein the bio-signal represents eye movement and/or brain activity signals.

18. The communication system according to claim 4, wherein the bio-signal represents eye movement and/or brain activity signals.

* * * * *